United States Patent
Odell et al.

(10) Patent No.: US 8,226,616 B2
(45) Date of Patent: *Jul. 24, 2012

(54) SYRINGE ASSEMBLY

(75) Inventors: Robert B. Odell, Franklin Lakes, NJ (US); Lawrence J. Zach, Columbus, NE (US); Alex S. Wallace, Mahwah, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 91 days.

This patent is subject to a terminal disclaimer.

(21) Appl. No.: 12/782,787

(22) Filed: May 19, 2010

(65) Prior Publication Data

US 2010/0288663 A1    Nov. 18, 2010

Related U.S. Application Data

(60) Continuation of application No. 12/684,189, filed on Jan. 8, 2010, now Pat. No. 7,935,103, which is a division of application No. 10/727,194, filed on Dec. 3, 2003, now Pat. No. 7,682,342, which is a continuation of application No. 10/067,166, filed on Feb. 4, 2002, now abandoned, which is a continuation of application No. 09/060,117, filed on Apr. 14, 1998, now Pat. No. 6,361,524.

(51) Int. Cl.
*A61M 5/00* (2006.01)

(52) U.S. Cl. ......... 604/181; 604/187; 604/111; 206/365

(58) Field of Classification Search .................. 604/181, 604/187, 111; 206/365
See application file for complete search history.

(56) References Cited

U.S. PATENT DOCUMENTS

| | | | |
|---|---|---|---|
| 2,453,591 A | 11/1948 | Poux |
| 2,860,635 A | 11/1958 | Wilburn |
| 3,930,492 A | 1/1976 | Hatsuno et al. |
| 4,044,757 A | 8/1977 | McWhorter et al. |
| 4,826,483 A | 5/1989 | Molnar, IV |
| 4,906,231 A | 3/1990 | Young |

(Continued)

FOREIGN PATENT DOCUMENTS

EP    0329358    8/1989

(Continued)

OTHER PUBLICATIONS

Becton Dickinson and Company, Becton Dickinson Catalog 1993, Becton Dickinson Division, pp. B-2, B-3 (Nov. 1992).

(Continued)

*Primary Examiner* — Theodore Stigell
(74) *Attorney, Agent, or Firm* — Diehl Servilla LLC

(57) ABSTRACT

A syringe assembly comprises a syringe barrel having an elongated body defining a chamber for retaining fluid, an open proximal end, a distal end and a frusto-conically shaped tip extending from the distal end and having a passageway therethrough in fluid communication with the chamber. The chamber has an inside diameter of at least 13.5 mm. A stopper is in fluid-tight engagement inside the barrel. An elongated plunger rod extends proximally from the stopper through the open proximal end of the barrel. A flange is positioned at the proximal end of the plunger rod. The flange is shaped and positioned to limit the distal motion of the plunger rod in the barrel by contacting the proximal end of the barrel. A tip cap is releasably connected to the tip for sealing the passageway and the chamber contains injectable liquid.

20 Claims, 8 Drawing Sheets

U.S. PATENT DOCUMENTS

| | | | |
|---|---|---|---|
| 4,915,692 A | 4/1990 | Verlier | |
| 5,085,640 A | 2/1992 | Gibbs | |
| 5,090,962 A | 2/1992 | Landry, Jr. et al. | |
| 5,116,320 A | 5/1992 | Lo Duca | |
| 5,211,629 A | 5/1993 | Pressley et al. | |
| 5,242,405 A * | 9/1993 | Howe | 604/125 |
| 5,304,138 A | 4/1994 | Mercado et al. | |
| 5,308,322 A | 5/1994 | Tennican et al. | |
| 5,364,369 A | 11/1994 | Reynolds | |
| 5,370,620 A | 12/1994 | Shonfeld | |
| 5,395,339 A | 3/1995 | Talonn et al. | |
| 5,593,387 A | 1/1997 | Rupp | |
| 5,807,343 A | 9/1998 | Tucker et al. | |
| 5,817,064 A | 10/1998 | DeMarco et al. | |
| 5,820,603 A | 10/1998 | Tucker et al. | |
| 5,899,889 A | 5/1999 | Futagawa et al. | |
| 6,361,524 B1 * | 3/2002 | Odell et al. | 604/187 |
| 6,743,216 B2 | 6/2004 | Odell et al. | |
| 7,682,342 B2 * | 3/2010 | Odell et al. | 604/181 |

FOREIGN PATENT DOCUMENTS

| | | |
|---|---|---|
| FR | 2622804 | 11/1987 |
| GB | 584841 | 1/1947 |
| GB | 2197792 | 6/1988 |
| WO | WO-95/28978 | 11/1995 |
| WO | WO-98/56440 | 12/1998 |

OTHER PUBLICATIONS

Machine Translation of FR-2622804, 5 pgs.

Non-Final Office Action in U.S. Appl. No. 12/684,189, dated Jul. 13, 2010, 10 pgs.

* cited by examiner

SYRINGE ASSEMBLY

CROSS-REFERENCE TO RELATED APPLICATIONS

This is a continuation of U.S. patent application Ser. No. 12/684,189, filed on Jan. 8, 2010, which is a division of U.S. patent application Ser. No. 10/727,194, filed on Dec. 3, 2003, now U.S. Pat. No. 7,682,342, issued Mar. 23, 2010, which is a continuation of U.S. patent application Ser. No. 10/067,166, filed on Feb. 4, 2002, now abandoned, which is a continuation of U.S. patent application Ser. No. 09/060,117, filed on Apr. 14, 1998, now U.S. Pat. No. 6,361,524, issued Mar. 26, 2002.

BACKGROUND OF THE INVENTION

The present invention relates to syringe assemblies and more particularly concerns syringe assemblies for use in I.V. flush procedures.

An I.V. catheter is a commonly used therapeutic device. Many patients, in accordance with their therapy, have an I.V. catheter connected to a vein ready for use in various procedures or in fluid communication with an I.V. system for infusing liquids and medication. Many I.V. sets have I.V. ports which are in fluid communication with a catheter and allow access for the purpose of injecting medication into the patient, and for use in flushing techniques to maintain catheter patency and integrity. Healthcare facilities have flushing protocols which depend on the amount of time the catheter will remain in the patient and the type of catheter being used. For example, a peripherally inserted central catheter (PICC) is a long flexible catheter, which is typically inserted into the central venous system (optimally with the tip terminating in the superior vena cava) via the superficial veins of the antecubital fossa. PICC lines are designed for use when intermediate or long-term therapy is prescribed. These catheter lines must be periodically flushed with saline flush solution and/or heparin lock flush solution depending on the protocol. Among other things, flushing saline solution removes blood from the catheter and heparin helps prevent the formation of future blood clots. The most common I.V. ports are covered by pierceable septums or pre-slit septums and are known in the art and sometimes referred to as "PRN" from the Latin pro re nata meaning "as the need arises". The septum is preferably made of rubber or another elastomeric material which permits insertion of a sharp needle cannula in order to infuse fluids into or to withdraw fluids from the catheter. Upon withdrawal of the needle cannula the septum seals itself. Ports having pre-slit septums are used with blunt cannula. Typically, the blunt cannula is attached to a syringe and the syringe is moved to place a gentle pressure on the pre-slit septum which is forced open by the blunt cannula to establish fluid communication. Also, some I.V. sets have access valves which are responsive to the frusto-conically shaped tip of a syringe barrel for allowing fluid communication between the interior of the syringe and the catheter.

Catheters are flushed using syringe assemblies filled with various fluids. In some cases, different fluids are injected sequentially in accordance with the protocol. For example, a saline solution followed by an anticoagulant such as heparin. The size of the syringe used to flush I.V. lines varies by various factors including the size and length of the catheter. Typically syringes of 1 ml, 3 ml, 5 ml and 10 ml volume are used. A commercially available 1 ml syringe may have a barrel inside diameter of approximately 6.6 mm (0.26 inch), a 3 ml syringe may have a barrel inside diameter of approximately 8.6 mm (0.34) inch while a 10 ml syringe may have a barrel inside diameter of approximately 14.5 mm (0.57 inch). Unfortunately, during the flushing of vascular access devices, different nominal size syringes generate substantially different pressures in the solution being injected by the same force being applied to the syringe plunger rod. For example, a ten-pound force on the plunger rod may cause a 10 ml syringe to generate 40 psi of liquid pressure while a 3 ml syringe generates 110 psi and a 1 ml syringe generates 190 psi.

Control of pressure is very important during flush procedures for detection of resistance to flow or catheter occlusion, and to avoid over-pressure because of the danger of dislodging a clot or rupturing the catheter. Accordingly, many practitioners are believed to prefer the 10 ml size syringe because when using the 10 ml syringe it is easier to observe possible catheter occlusion and it is less likely to provide excessive pressures which could dislodge a blood clot or damage the catheter.

Also, it is important in the flush procedure not to draw blood back into the catheter where it can clot and seal the catheter. In order to prevent blood reflux into the catheter the user is encouraged to maintain a positive pressure in the line during the flush procedure. This may involve slowly withdrawing the syringe and cannula from the I.V. port while still applying pressure to the syringe plunger rod. When using a syringe with an elastomeric stopper, if the stopper is compressed by action of the plunger rod, release of the plunger rod causes the stopper to expand and may cause blood to enter the catheter line.

Although a wide variety of catheters and I.V. ports can be adequately flushed using currently available syringe assemblies, there is still a need for simple, straight forward easy-to-manufacture syringe assemblies which eliminate the substantial pressure variations possible with the present syringes and minimize the potential for accidentally drawing blood in the catheter during the flush procedure.

SUMMARY OF THE INVENTION

A syringe assembly comprises a syringe barrel having an elongated body defining a chamber for retaining fluid, an open proximal end, a distal end and a frusto-conically shaped tip extending from the distal end having a tip passageway therethrough in fluid communication with the chamber. The chamber has an inside diameter of at least 13.5 mm (0.53 inch). The chamber has a distal end defined by a distal wall through which the passageway passes. A stopper is in fluid communication with the inside of the barrel. An elongated rigid plunger rod extends proximally from the stopper through the open proximal end of the barrel and contains a flange at its proximal end. The flange is shaped and positioned to limit the distal motion of the plunger rod in the barrel by contacting the proximal end of the barrel. A tip cap is releasably connected to the tip for sealing the passageway and the chamber contains injectable liquid.

In another embodiment the stopper and the plunger rod are dimensioned so that when the plunger rod flange contacts the proximal end of the barrel there is a space between at least a portion of the distal end of the stopper and the distal wall of the syringe barrel.

In another embodiment, a syringe assembly comprises a syringe barrel having an elongated body defining a chamber for retaining fluid, an open proximal end, a distal end and a frusto-conically shaped tip extending from the distal end and having a tip passageway therethrough in fluid communication with the chamber. The chamber has an inside diameter of at least about 13.5 mm (0.53 inch). The chamber has a distal end defined by a distal wall through which the passageway passes.

The length of the chamber is no more than about 57 mm (2.25 inches). A stopper is in fluid-tight communication with the inside of the barrel. An elongated plunger rod extends proximally from the stopper through the open proximal end of the barrel. In this embodiment the plunger rod does not necessarily have a flange on its proximal end, and the plunger rod flange does not necessarily limit the distal motion of the plunger rod in the barrel.

DETAILED DESCRIPTION OF THE INVENTION

Figure 1:
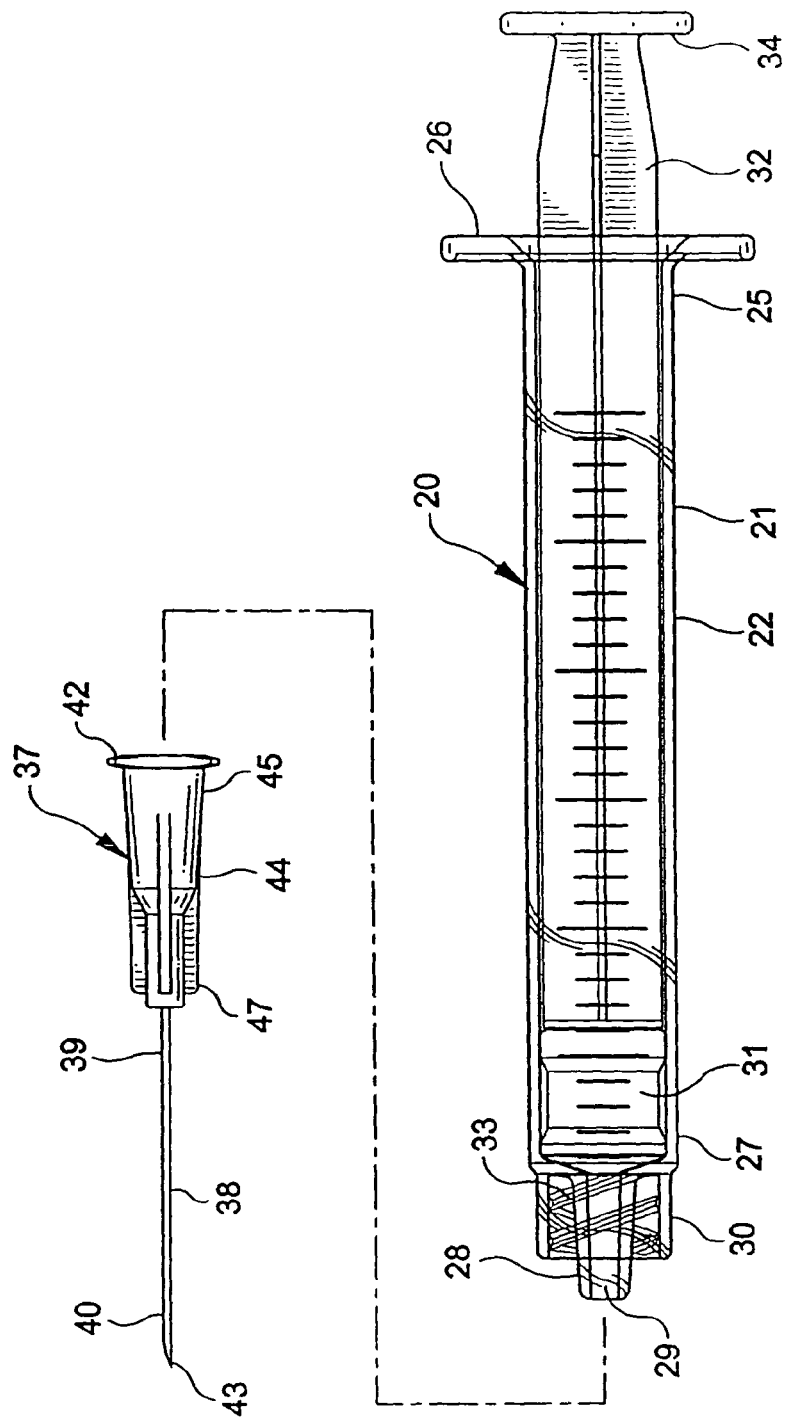
FIG. 1 is an exploded view illustrating a prior art syringe assembly and needle assembly.

While this invention is satisfied by embodiments in many different forms, there are shown in the drawings and will herein be described in detail, preferred embodiments of the invention with the understanding that the present disclosure is to be considered exemplary of the principles of the invention and not intended to limit the invention to the embodiments illustrated. The scope of the invention will be measured by the appended claims and their equivalents.

Adverting to FIGS. 1-7, prior art syringe assembly 20 includes a barrel 21 having an elongate body 22 defining a chamber 23 for retaining fluid. The barrel includes an open proximal end 25 having a flange 26 and a distal end 27 including a tip 28 having a passageway 29 therethrough in fluid communication with the chamber. The distal end of the barrel also preferably, but not necessarily, includes a locking luer-type collar 30 concentrically surrounding tip 28. The luer collar has an internal thread 33.

A prior art needle assembly includes a cannula 38 having a proximal end 39, a distal end 40 and a lumen therethrough. The distal end of the cannula may include a sharp tip 43 or a blunt tip (not illustrated). A hub 44 includes an open proximal end 45 containing a cavity and a distal end 47 attached to proximal end 39 of cannula 38 so that the lumen of the cannula is in fluid communication with the cavity in the hub. The needle assembly is attached to the syringe through frictional engagement of the interior surface of the cavity and the exterior surface of tip 28. The hub also includes radial projections 42 on its proximal end for engaging thread 33 to hold it securely to the barrel. Prior art syringe assembly 20 further includes a resilient stopper 31 connected to an elongated plunger rod 32 having a flange 34 at its proximal end.

The most commonly used 3 ml syringe in the United States has a barrel inside diameter of approximately 8.6 mm (0.34 inch). As best illustrated in FIG. 1, the length of its plunger rod and stopper is longer than the chamber in the barrel so that portions of the plunger rod and the plunger rod flange extend proximally from the open proximal end of the barrel when the stopper has reached its maximum distal position and is resting on the interior distal wall of the chamber. Further, the barrel flange is not non-circularly shaped while the plunger rod flange is circularly shaped so that the plunger rod flange extends radially beyond the outside of the barrel flange to facilitate drawing the plunger rod and stopper in a proximal direction to fill the syringe using known methods.

In use, the prior art 3 ml syringe assembly is connected to a hypodermic needle assembly and filled with flush solution using known methods. For example, the syringe with needle assembly attached is used to pierce the pierceable stopper of a vial containing flush solution and the flush solution is drawn into the syringe barrel by pulling plunger rod flange 34 in a proximal direction while holding barrel 21, to draw fluid through the needle cannula into the chamber of the syringe barrel.

Figure 2:
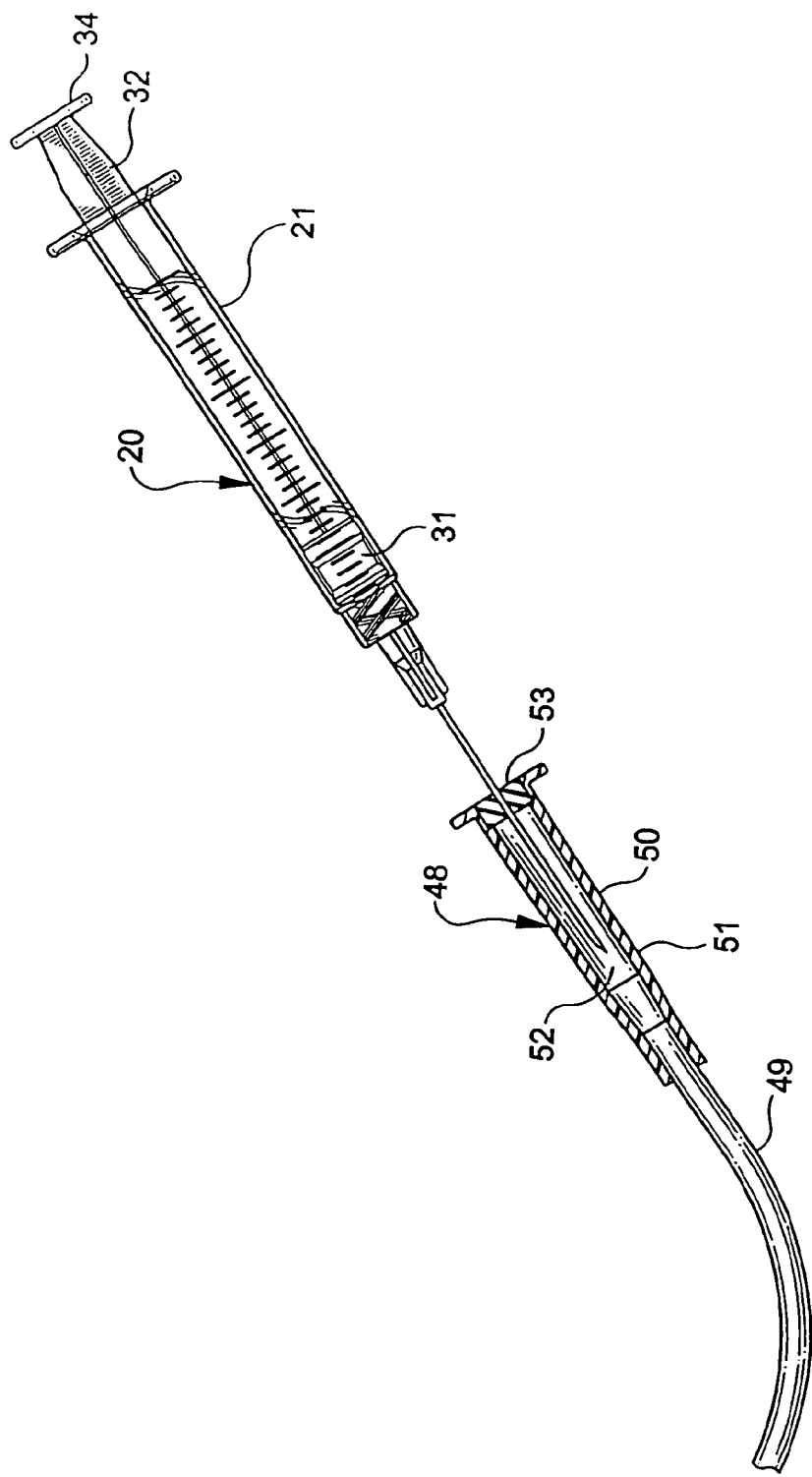
FIG. 2 illustrates a prior art syringe and needle assembly being used to flush an I.V. site and catheter.
Figure 3:
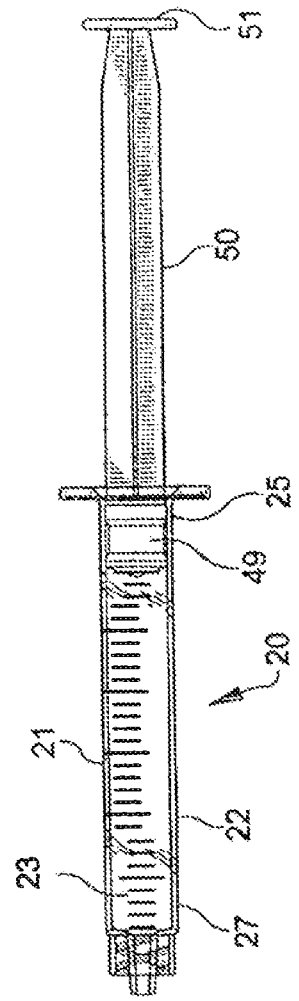
FIG. 3 illustrates the prior art syringe of FIG. 1 with the plunger rod and stopper in their most proximal position simulating a syringe full of liquid for injection.
Figure 4:
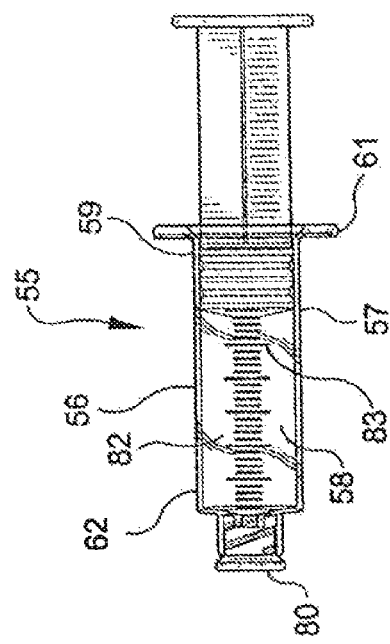
FIG. 4 illustrates the syringe assembly of the present invention.
Figure 5:
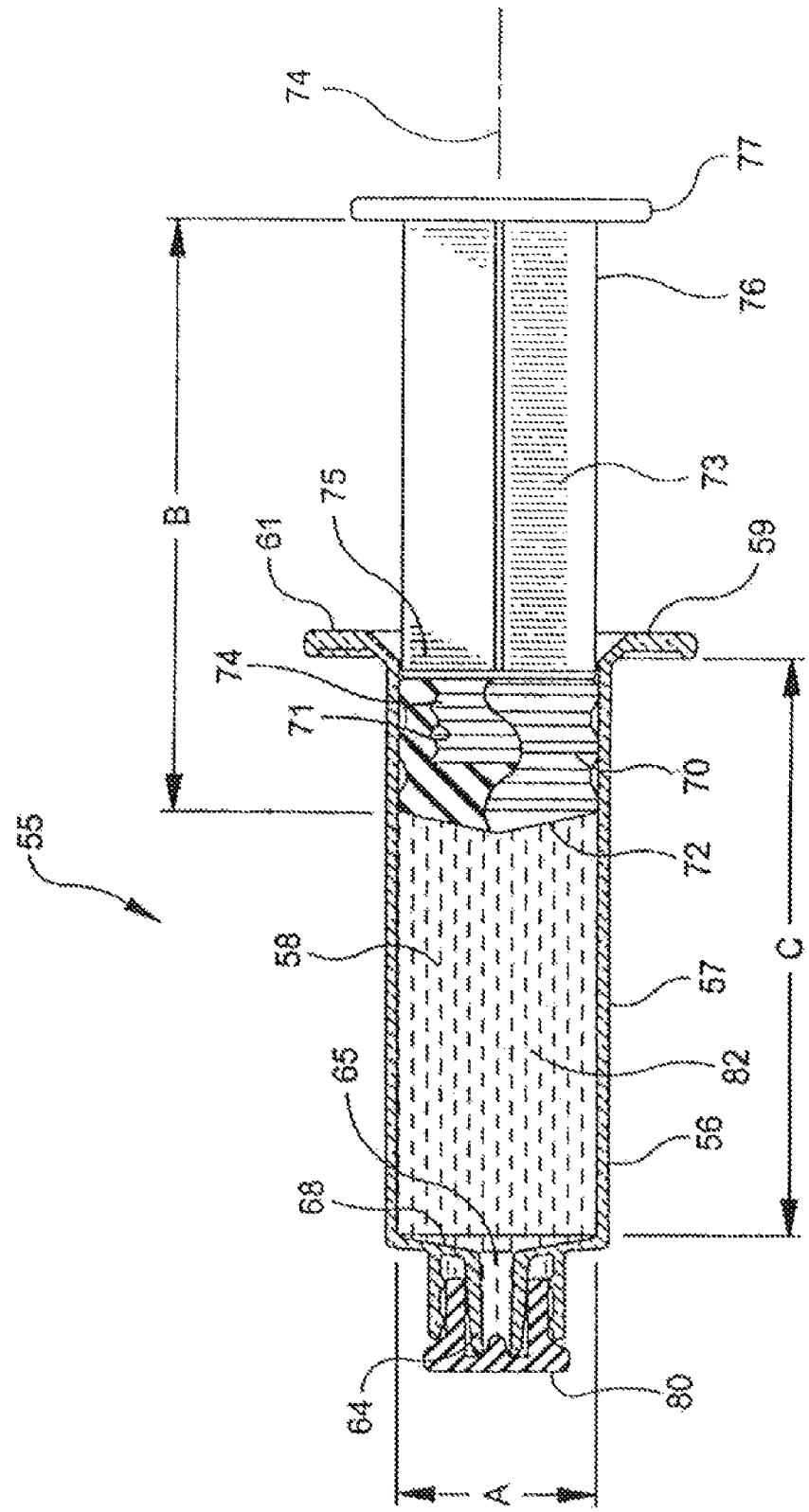
FIG. 5 is en enlarged partially cross-sectioned view of the syringe assembly of FIG. 4.

I.V. sets can be very complicated and include multiple injection ports, a valve and other components. For the purpose of illustrating the present invention a simplified I.V. set 48 is illustrated in FIG. 2. I.V. set 48 comprises an I.V. site 51 which includes a housing 50 having a hollow interior conduit 52 and a septum 53 at its proximal end. A catheter 49 having a lumen therethrough extends from the distal end of the housing.

The filled prior art syringe is now ready for use in flushing a catheter. With the embodiment illustrated, sharp tip 43 of cannula 38 is moved to pierce septum 53 to establish fluid communication between the hollow interior conduit 52 of housing 51 and the chamber of the syringe barrel. The syringe is held so that the liquid in the chamber can be forced into the hollow interior conduit of the housing and through the catheter by applying digital pressure, such as with the use of the thumb, to flange 34 to move the plunger rod in a distal direction with respect to the barrel. Due to the relatively small diameter of the syringe barrel the user must be careful not to exert excess pressure which could dislodge a blood clot or damage the catheter. Also, it is important to maintain a positive pressure during the flush procedure so that when the syringe is nearly empty, the user should begin to withdraw the cannula from the septum as the fluid is being expelled. The prior art syringe has a disadvantage when being used as a flush syringe since the length of the plunger rod is so long that the elastomeric stopper can be compressed when it contacts the distal end of the chamber in the barrel. If the user compresses the stopper and then relieves the pressure on the plunger rod flange the stopper will expand back to its normal size drawing liquid from the catheter into the syringe barrel. This is undesirable since this event can cause blood to undesirably enter the catheter at the catheter distal end.

A syringe assembly 55 of the present invention preferably includes a syringe barrel 56 having an elongated body 57 defining a chamber 58 for retaining fluid. The syringe barrel includes an open proximal end 59 having a barrel flange 61, a distal end 62 and a frusto-conically shaped tip 64 extending from the distal end and having a tip passageway 65 therethrough in fluid communication with the chamber. The inside diameter A of the chamber is at least 13.5 mm (0.53 inch). Chamber 58 includes a distal end defined by distal chamber wall 68. The length of the chamber is illustrated as element C in FIG. 5 and is measured approximately between the distal chamber wall and the proximal end of the chamber. The chamber is the generally constant diameter of constant cross-section portion of the inside of the barrel. Although a wide variety of chamber lengths are within the purview of the present invention, the preferred embodiment has a chamber length C which is no more than about 57 mm (2.25 inches) with a chamber length of no more than about 44.5 mm (1.75 inches) to 38.1 mm (1.5 inches) being desirable for many applications. A stopper 70 is in fluid-tight engagement inside the barrel. An elongated plunger rod 73 having a distal end 75 and a proximal end 76 defining a longitudinal axis 74, extends proximally from the stopper through the open proximal end of the barrel. In this embodiment, the plunger rod and the stopper are separate elements. The stopper is preferably made of an elastomeric material selected from the group of natural rubber, synthetic rubber, thermoplastic elastomers or combinations thereof. The plunger is preferably made of a rigid thermoplastic material. Plunger rod 73 includes a distally directed threaded extension 74 which engages a threaded recess 71 in stopper 70. In this embodiment, the syringe may be assembled without the plunger rod for purposes such as conserving space or reducing packaging material, and the plunger rod may be assembled to the stopper at the time of use by simply screwing the plunger rod into the stopper.

There are many ways to connect the stopper to a plunger rod including snap-fit structure, adhesives, welding and two-shot molding where a stopper of one material is molded with a plunger rod of another material. The threaded arrangement described hereinabove is considered exemplary of these many possibilities. It is also within the purview of the present invention to include a one-piece plunger rod and stopper assembly wherein the stopper and plunger rod are made of the same material.

The plunger rod also includes a plunger rod flange 77 at proximal end 76 of the plunger rod. As will be explained in more detail hereinafter, it is preferred that flange 77 is shaped and positioned to limit the distal motion of the plunger rod in the barrel by contacting the proximal end of the barrel rather than having the stroke of the plunger rod and stopper being limited by the stopper being compressed against distal chamber wall 68. Ideally, the flange should stop the forward motion of the stopper at the moment the distal face 72 of the stopper contacts distal chamber wall 68. When there is a space between at least a portion of the distal end or distal face of the stopper and the distal wall of the barrel. Since manufacturing tolerances will vary, it will be up to the manufacturer to choose whether there should be a gap between the stopper and the distal barrel wall or a slight stopper deflection when the plunger rod flange contacts the proximal end of the syringe barrel. In any event, it is not desirable to have excessive compression of the stopper which can, upon release of the plunger rod, draw blood into a catheter during a flush procedure.

A tip cap 80 is releasably connected to tip 28 sealing passageway 29. It is preferred that the tip cap is formed of material selected from the group of thermoplastic material and elastomeric material with elastomeric material being preferred. The syringe assembly of the present invention may contain volumes of fluid from about 1 ml to 10 ml wherein in the preferred embodiment contains no more than 3.3 ml of injectable liquid 82 in the chamber. It is preferred that the injectable liquid be selected from the group consisting of saline flush solution and heparin lock flush solution. These solutions are known in the art and readily available. An example of a saline flush solution is 0.9% Sodium Chloride USP. An example of a heparin lock flush solution is 0.9% Sodium Chloride with 100 USP units of Heparin Sodium per ml or 10 USP units of Heparin Sodium per ml.

The materials for the syringe barrel, the tip cap and the stopper will have to be chosen based not only on performance but on compatibility with the injectable liquid. In this preferred embodiment the syringe assembly is prefilled with injectable liquid. There may be a substantial amount of time between when the syringe assembly is filled and when the contents of the syringe assembly are delivered. Accordingly, materials chosen for the syringe assembly may have to be stable under long term storage.

The syringe assembly contains volume measuring indicia 83 on elongated body 57. The volume measuring indicia in the preferred embodiment shows volumes up to 3.0 ml. However, since the syringe assembly is preferably prefilled, the indicia may be limited to the exact amount of liquid in the syringe, for example, 3.0 ml. An important feature of the present invention over the smaller diameter 3 ml prior art syringes is that the larger diameter barrel provides a satisfactory area for printed or labeled instructions or a description of the syringe contents.

Figure 6:
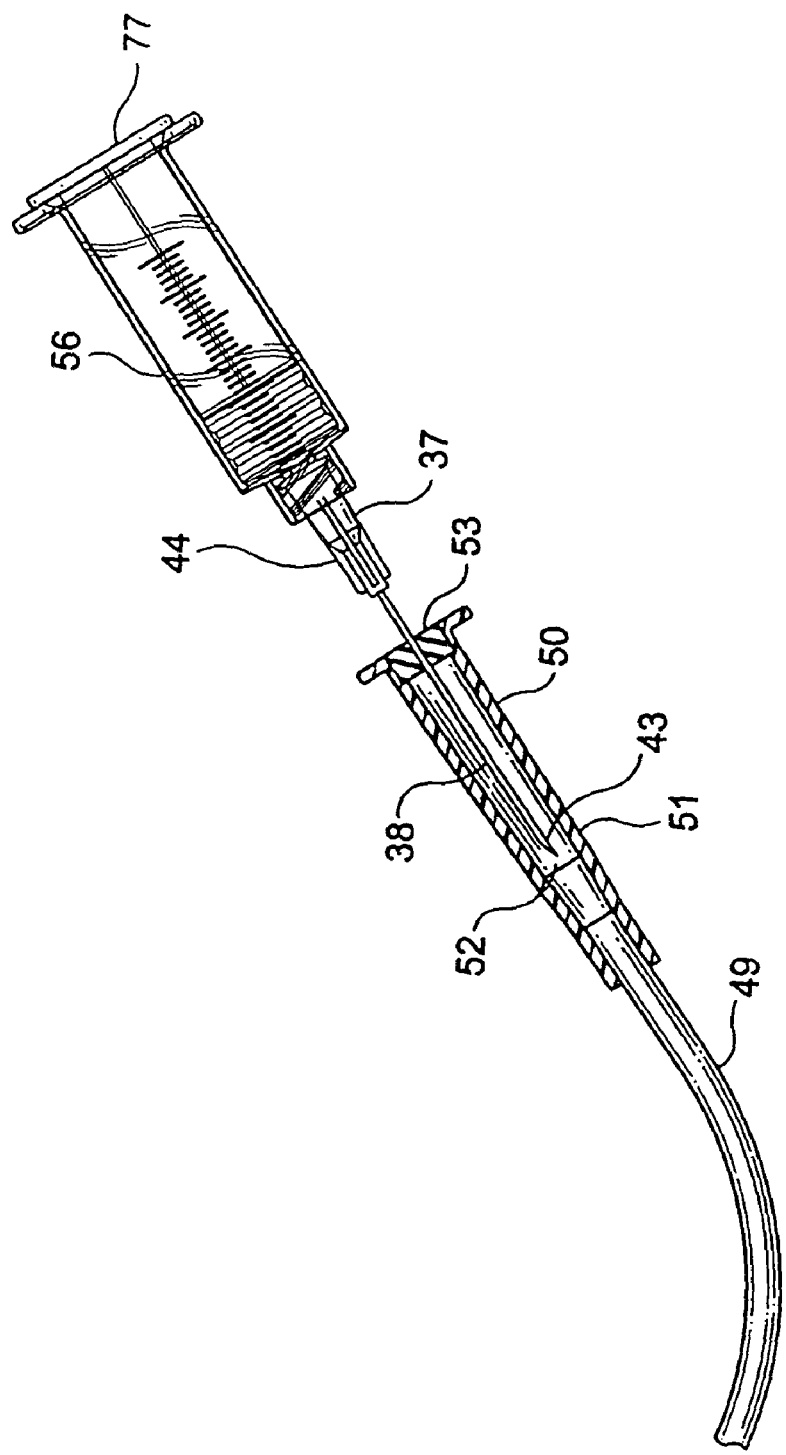
FIG. 6 illustrates the syringe assembly of FIG. 4 being used to flush an I.V. site and catheter.

Syringe assembly 55 can be used to flush catheters having I.V. sites in a manner similar to that described above for the prior art syringe. However, there are several major differences and advantages in using the syringe assembly of the present invention. To use syringe assembly 55 in a flushing procedure, the user first removes the tip cap and applies a needle assembly such as needle assembly 37 or a needle assembly having a blunt tip if the I.V. site has a pre-slit septum. Also, in I.V. sites having a valve, the user removes the tip cap and applies the syringe directly to the valve. Syringe assembly 55 is illustrated in FIG. 6 as being used with needle assembly 37 and I.V. site 50. When the needle assembly is applied to the syringe barrel the assembled unit is moved in position so that sharp tip 43 of the needle will penetrate septum 53 and enter hollow internal conduit 52 of housing 51.

The user now advances the plunger rod in the distal direction by applying digital pressure to flange 77 to expel the contents of the syringe into and through the catheter. A major advantage of the syringe assembly of the present invention is that the fluid pressure will be only about one-third of the fluid pressure if a prior art 3 ml syringe were being used with the same force being applied to the plunger rod. The reduced pressure makes it easier for the user to determine if the catheter is open and reduces the possibility of dislodging a clot or rupturing the catheter. Also, if larger volume syringes having the same diameter are used, the general feel of the syringe and the technique will remain consistent from syringe to syringe so that the feel and the touch and the forces applied in flushing the catheter with the 3 ml syringe of the present invention are the same as a 10 ml syringe having the same diameter.

Figure 7:
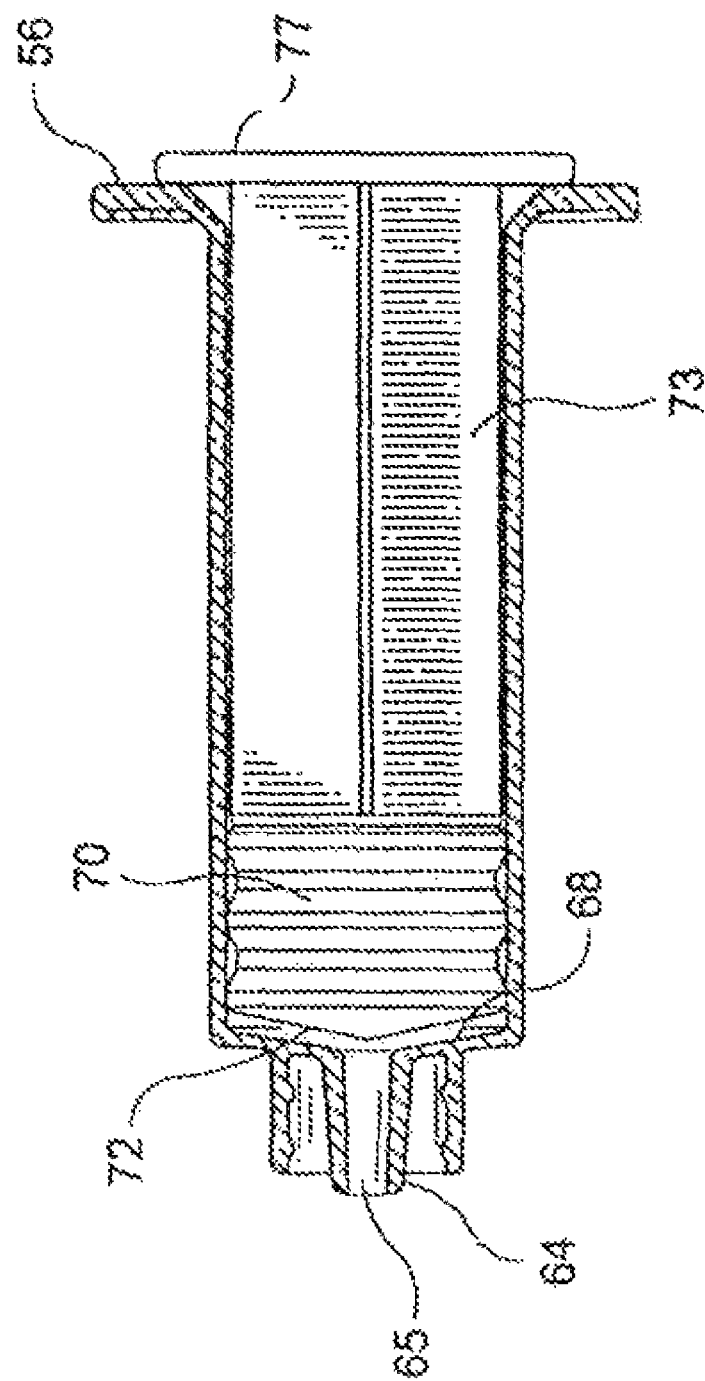
FIG. 7 is an enlarged cross-sectional view of the syringe assembly of the present invention illustrating the syringe assembly after use.

A further advantage of the present invention, as best illustrated in FIGS. 6 and 7 is that the distal motion of the plunger rod is limited by flange 77 contacting distal end 59 of the barrel.

As previously mentioned, it is important to maintain a positive pressure in the intravenous line to prevent blood reflux into the catheter lumen. This can be conveniently achieved by partial withdrawal of the cannula from the septum during the injection of the final volume of injectable liquid. It is an important advantage of the present invention that it maintains positive pressure in the line for two reasons. First, at the end of the fluid delivery plunger rod flange 77 is in contact with the proximal end of the syringe barrel and is not sticking out or spaced from the proximal end of the barrel as with the prior art syringe as illustrated in FIG. 1. Therefore, inadvertent or accidental movement of the plunger rod in a proximal direction, to create negative pressure in the line, is avoided. In this preferred embodiment, the plunger rod flange 77 is sized and shaped to be smaller than barrel flange 61 in all dimensions measured radially from the longitudinal axis of the plunger rod. Accordingly, the plunger rod flange cannot be pulled back at the end of its stroke. Many prior art syringes contain a round plunger rod flange and an oblong or non-circular barrel flange so that even when the plunger rod flange is close to the barrel flange it still is larger in a radial direction for easy movement of the plunger rod in a proximal direction with respect to the barrel. However, since the syringe assembly of the present invention is preferably prefilled there is no need for having such ready access to the plunger rod flange.

Secondly, as can be seen in FIG. 7 when plunger rod flange 77 is in contact with proximal end 56 of the syringe barrel distal end or distal face 72 of the stopper is spaced from distal chamber wall 68 of the syringe barrel. This configuration prevents the stopper from being excessively compressed against distal chamber wall 68. If the plunger rod is long enough to allow substantial compression of the stopper release of the force on the plunger rod will allow the stopper to expand and possibly pull fluid back from the catheter and allow blood to enter the catheter tip. In this embodiment it is preferred that the effective length B of the stopper and the plunger rod is measured from the distal side of plunger rod flange 77 to distal end 72 of the stopper shall be 51 mm (2.0 inch) or less.

Accordingly, the syringe assembly of the present invention has two major advantages over prior art syringes in that its large diameter, never before available in a 3 ml syringe, reduces the pressures associated with flushing an I.V. catheter thereby making it easier for the user to detect a clot and less likely that the fluid pressures will damage the catheter. Further, refluxing is prevented or substantially minimized by having a plunger rod flange which limits the stroke of the plunger rod and the stopper assembly so that the stopper cannot be substantially compressed on the distal syringe barrel wall which may cause refluxing of fluid and blood into the catheter.

Syringe assembly 55 may be provided in a tearable or frangible package which provides a tamper evident barrier surrounding the syringe assembly. Materials such as paper coated paper, plastic film, foil and combinations thereof can be used for such purposes. Tearing of the package may be evidence that the syringe has been used or tampered with. Syringe assembly 55 may also be provided in a package which provides a sterile barrier surrounding the syringe assembly. A package which constitutes a sterile barrier which provides substantial resistance to the passage of microorganisms can be made of many known materials such as paper, coated paper, plastic film, foil, non-woven materials and combinations thereof. If the package is made of appropriate tearable or frangible materials it can function as a sterile barrier and as a tamper evident package. In making the packaged syringe assembly, syringe assembly 55 can be sterilized after filling and placed in the package or placed in the package and sterilized or sterilized, placed in the package and sterilized a second time.

Figure 8:
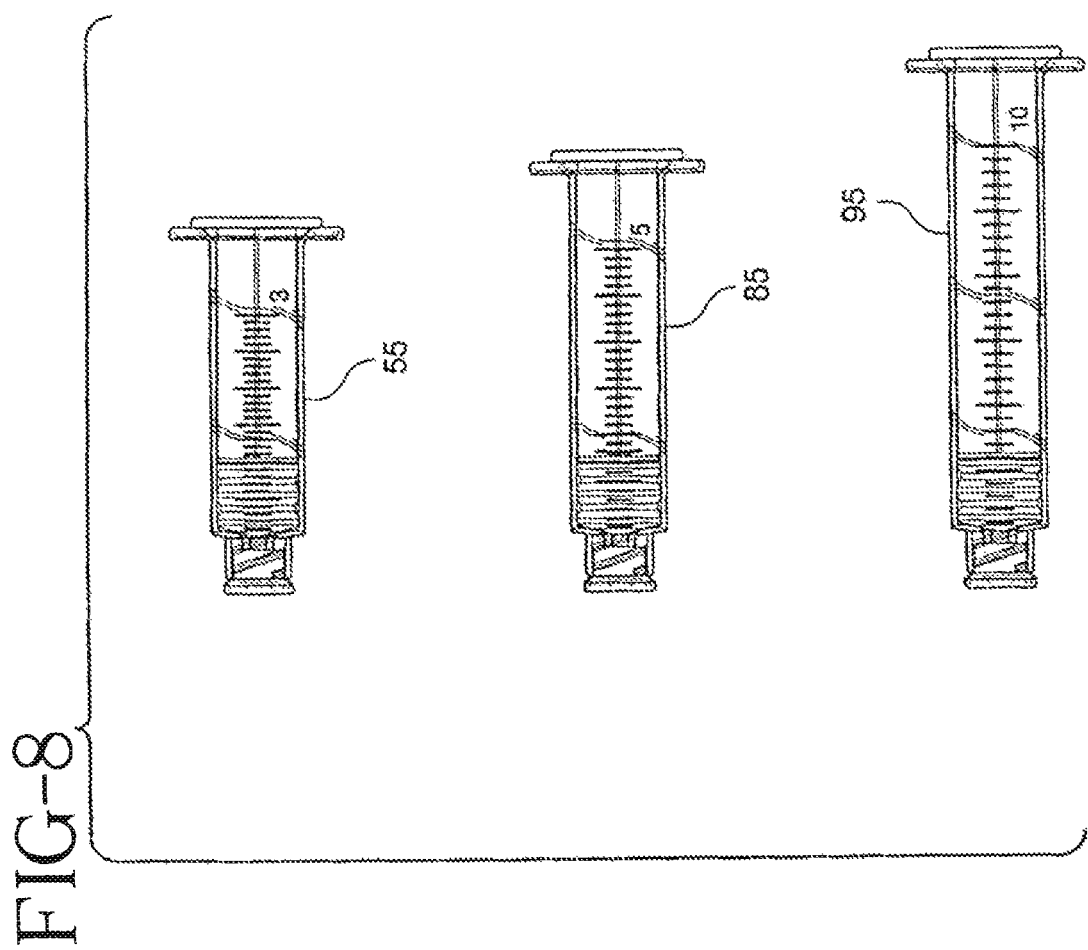
FIG. 8 illustrates a family of syringes of the present invention having three volumes of 3 ml, 5 ml and 10 ml.

In addition to the preferred syringe assembly 55 of the present invention, as illustrated in FIG. 8, other embodiments of the present invention include a syringe assembly 85 having a capacity of about 5 ml and a syringe assembly 95 having a capacity of about 10 ml. All three syringe assemblies have an inside diameter of at least about 13.5 mm (0.53 inch).

Figure 9:
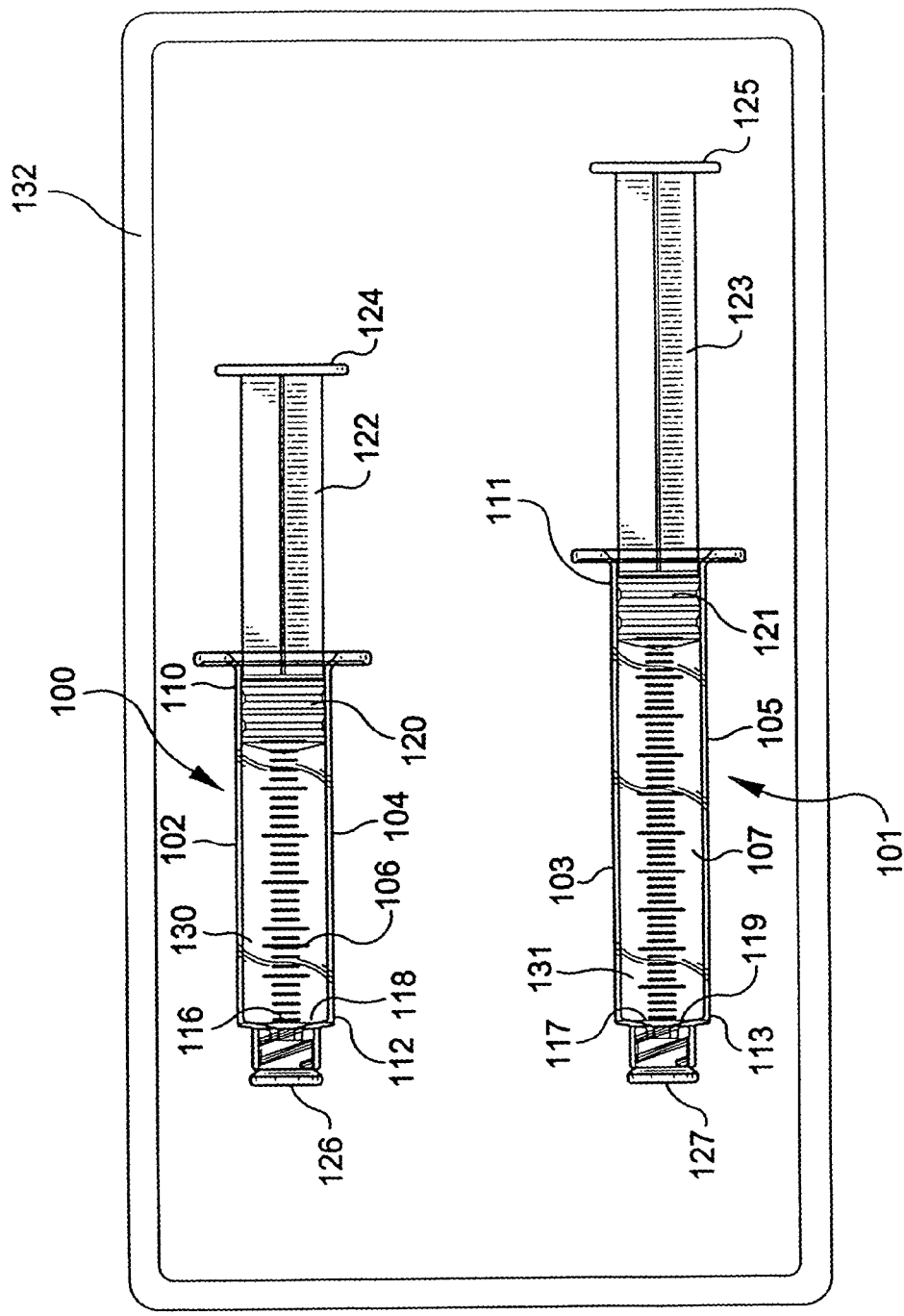
FIG. 9 illustrates a kit containing two syringe assemblies of the present invention in a package which acts as a sterile barrier.

Referring to FIG. 9, a catheter flush kit comprises a first syringe assembly 100 and a second syringe assembly 101. Each of the syringe assemblies includes a syringe barrel (102, 103) having an elongated body (104, 105) defining a chamber 106, 107 for retaining fluid. Each syringe barrel includes an open proximal end 110, 111, a distal end 112, 113 and a frusto-conically shaped tip extending from the distal end and having a tip passageway 116 and 117, therethrough in fluid communication with chambers 106 and 107. Each chamber has an inside diameter of at least 13.5 mm (0.53 inch) and a distal end defined by a distal wall 118 and 119 through which the passageways pass. A stopper 120 and 121 is in fluid-tight engagement inside each barrel. Elongated plunger rods 122, 123 define a longitudinal axis and extend proximally from the stoppers through the open ends of the barrels. Flanges 124 and 125 are positioned at the proximal ends of plunger rods 122 and 123. A tip cap 126 and 127 seals the passageway of each syringe. First syringe 100 has no more than about 3.3 ml of a first injectable liquid 130 in chamber 106. The second syringe assembly has no more than about 10 ml of a second injectable liquid 131 in chamber 107. The injectable liquids are selected from the group consisting of saline flush solution and heparin lock solution. Syringe assemblies 100 and 101 are contained in a package 132 which preferably provides a tamper evident barrier surrounding the syringe assemblies. The plunger rod flange in at least one of the syringe assemblies is shaped and positioned to limit the distal motion of the plunger rod in the barrel by contacting the proximal end of the barrel.

What is claimed is:

1. An I.V. flush syringe assembly comprising:
    a syringe barrel having an elongated body defining a chamber for retaining fluid, an open proximal end, a distal end and a frusto-conically shaped tip extending from said distal end having a tip passageway therethrough in fluid communication with said chamber, said chamber having an inside diameter of at least 13.5 mm (0.53 inch), said chamber having a distal end defined by a distal wall through which said passageway passes, the length of said chamber being no more than 57 mm (2.25 inches);
    a stopper in fluid-tight engagement inside said barrel;
    an elongated rigid plunger rod defining a longitudinal axis and extending proximally from said stopper through said open proximal end of said barrel, a flange at a proximal end of said plunger rod;
    a tip cap releasably connected to said tip for sealing said passageway; and
    flush solution in said chamber, wherein the fluid pressure in the flush solution injected through said passageway when force is applied to the plunger rod is about one-third of the fluid pressure in a flush solution injected through a passageway of a 3 ml syringe barrel having an inside diameter of about 8.6 mm when the same force is applied to the plunger rod.

2. The syringe assembly of claim 1, wherein the length of said chamber is less than about 57 mm (2.25 inches).

3. The syringe assembly of claim 2, wherein the length of said chamber is in the range of 38.1 mm (1.5 inches) to 44.5 mm (1.75 inches).

4. The syringe assembly of claim 1 wherein said chamber contains no more than 3.5 ml of flush solution.

5. The syringe assembly of claim 1 wherein said syringe assembly is contained in a package which provides a barrier surrounding the syringe assembly, the barrier selected from one of a tamper evident barrier and a sterile barrier.

6. The syringe assembly of claim 1 further including volume measuring indicia on said barrel.

7. The syringe assembly of claim 6, wherein said volume measuring indicia indicates the stopper position for a chamber volume of about 3 ml.

8. The syringe assembly of claim 1, wherein said inside diameter of said chamber is approximately 14.5 mm (0.57 inch).

9. The syringe assembly of claim 1 wherein said plunger rod flange is smaller than said open proximal end of said barrel when measured in a direction perpendicular to said longitudinal axis so that said plunger rod flange does not extend radially beyond said barrel.

10. The syringe assembly of claim 9 wherein said stopper and said plunger rod are dimensioned so that when said plunger rod flange contacts said proximal end of said barrel there is a space between at least a portion of the distal end of said stopper and said distal wall of said barrel.

11. The syringe assembly of claim 1 wherein said plunger rod includes a threaded extension projecting from a distal end of said plunger rod and said stopper defines a threaded recess which engages with said threaded extension of said plunger rod.

12. An I.V. flush syringe assembly comprising:
   a syringe barrel having an elongated body defining a chamber for retaining fluid, an open proximal end, a distal end and a frusto-conically shaped tip extending from said distal end having a tip passageway therethrough in fluid communication with said chamber, said chamber having an inside diameter of at least 13.5 mm (0.53 inch), said chamber having a distal end defined by a distal wall through which said passageway passes, the length of said chamber being no more than 57 mm (2.25 inches);
   a stopper in fluid-tight engagement inside said barrel;
   an elongated rigid plunger rod defining a longitudinal axis and extending proximally from said stopper through said open proximal end of said barrel, a flange at a proximal end of said plunger rod;
   a tip cap releasably connected to said tip for sealing said passageway; and
   flush solution in said chamber in an amount less than 10 ml, wherein the fluid pressure in the flush solution injected through said passageway when force is applied to the plunger rod is substantially the same as the fluid pressure in a flush solution in an amount of 10 ml injected through said passageway when the same force is applied to the plunger rod.

13. The syringe assembly of claim 12, wherein the syringe barrel comprises a barrel flange with a first dimension, the flange of the plunger rod having a second dimension that is smaller than the first dimension.

14. The syringe assembly of claim 12, wherein the flange of the plunger rod does not limit motion of the plunger rod in the barrel in a distal direction.

15. The syringe assembly of claim 12, wherein the plunger rod is attached to the stopper and the length of the plunger rod and the stopper is 51 mm (2.0 inches) or less.

16. The syringe assembly of claim 12, wherein the flush solution is present in an amount in the range from about 1 ml to about 5 ml.

17. The syringe assembly of claim 12, wherein the flush solution is present in an amount of 3.3 ml or less.

18. A syringe barrel having an elongated body defining a chamber for retaining fluid, an open proximal end, a distal end and a frusto-conically shaped tip extending from said distal end having a tip passageway therethrough in fluid communication with said chamber, said chamber having an inside diameter of at least 13.5 mm (0.53 inch), said chamber having a distal end defined by a distal wall through which said passageway passes, the length of said chamber being no more than 57 mm (2.25 inches), the chamber containing flush solution in an amount less than 10 ml.

19. The syringe barrel of claim 18, wherein said syringe barrel is contained in a package which provides a barrier surrounding the syringe assembly, the barrier selected form one of a tamper evident barrier and a sterile barrier.

20. The syringe assembly barrel of claim 18, further comprising volume measuring indicial.

\* \* \* \* \*